(12) United States Patent
Yamaoka

(10) Patent No.: US 10,161,918 B2
(45) Date of Patent: Dec. 25, 2018

(54) ULTRASONIC FLAW DETECTOR AND METHOD OF OPERATING ULTRASONIC FLAW DETECTOR

(71) Applicant: KAWASAKI JUKOGYO KABUSHIKI KAISHA, Kobe-shi, Hyogo (JP)

(72) Inventor: Toshihiro Yamaoka, Nagoya (JP)

(73) Assignee: KAWASAKI JUKOGYO KABUSHIKI KAISHA, Kobe-shi (JP)

( * ) Notice: Subject to any disclaimer, the term of this patent is extended or adjusted under 35 U.S.C. 154(b) by 306 days.

(21) Appl. No.: 14/915,389

(22) PCT Filed: Aug. 27, 2014

(86) PCT No.: PCT/JP2014/004406
§ 371 (c)(1),
(2) Date: Feb. 29, 2016

(87) PCT Pub. No.: WO2015/029428
PCT Pub. Date: Mar. 5, 2015

(65) Prior Publication Data
US 2016/0209375 A1 Jul. 21, 2016

(30) Foreign Application Priority Data
Aug. 30, 2013 (JP) .................. 2013-179632

(51) Int. Cl.
*G01N 29/30* (2006.01)
*G01N 29/04* (2006.01)
*G01N 29/22* (2006.01)
(Continued)

(52) U.S. Cl.
CPC ............. *G01N 29/30* (2013.01); *G01N 29/04* (2013.01); *G01N 29/043* (2013.01);
(Continued)

(58) Field of Classification Search
CPC .................................................. G01N 29/30
See application file for complete search history.

(56) References Cited

U.S. PATENT DOCUMENTS

2004/0244491 A1 12/2004 Vyas et al.
2009/0178465 A1 7/2009 Ethridge et al.
(Continued)

FOREIGN PATENT DOCUMENTS

CA 1204851 A 5/1986
JP S63-256851 A 10/1988
(Continued)

OTHER PUBLICATIONS

Mar. 7, 2017 Extended Search Report issued in European Patent Application No. 14840208.4.
(Continued)

*Primary Examiner* — Robert R Raevis
(74) *Attorney, Agent, or Firm* — Oliff PLC

(57) ABSTRACT

An ultrasonic device includes: a first and second flaw detection head; a moving mechanism that causes the first flaw detection head and the second flaw detection head to perform scanning; a calibration area in which a calibration standard sample is disposed; a flaw detection area in which an inspection object is disposed; and a controller that performs a first calibration process or a second calibration process, the first calibration process being a process of causing the first flaw detection head to scan the calibration standard sample to perform calibration using the calibration standard sample, the second calibration process being a process of causing the second flaw detection head to scan the calibration standard sample to perform calibration using the calibration standard sample when performing a first flaw detection process of performing ultrasonic flaw detection inspection of the inspection object by the first flaw detection head.

19 Claims, 10 Drawing Sheets

(51) Int. Cl.
  *G01N 29/265* (2006.01)
  *G01N 29/275* (2006.01)
(52) U.S. Cl.
  CPC ......... *G01N 29/225* (2013.01); *G01N 29/265* (2013.01); *G01N 29/275* (2013.01); *G01N 2291/015* (2013.01); *G01N 2291/0231* (2013.01); *G01N 2291/044* (2013.01); *G01N 2291/048* (2013.01); *G01N 2291/101* (2013.01); *G01N 2291/105* (2013.01); *G01N 2291/106* (2013.01); *G01N 2291/2632* (2013.01); *G01N 2291/2638* (2013.01); *G01N 2291/2694* (2013.01)

(56) References Cited

U.S. PATENT DOCUMENTS

2009/0178466 A1* 7/2009 Ethridge ................ G01N 29/07
                                                            73/1.86
2015/0253288 A1* 9/2015 Spencer ................ G01N 29/24
                                                            73/602

FOREIGN PATENT DOCUMENTS

| JP | H05-264207 A | 10/1993 |
| JP | H0611494 A | 1/1994 |
| JP | H06-27093 A | 2/1994 |
| JP | H07325071 A | 12/1995 |
| JP | H08-261997 A | 10/1996 |
| JP | H09113492 A | 5/1997 |
| JP | H11-326296 A | 11/1999 |
| JP | 2002-031623 A | 1/2002 |
| JP | 2009-506318 A | 2/2009 |
| WO | 2007/053100 A1 | 5/2007 |

OTHER PUBLICATIONS

Oct. 28, 2014 International Search Report issued in International Patent Application No. PCT/JP2014/004406.
Mar. 1, 2016 International Preliminary Report on Patentability issued in International Patent Application No. PCT/JP2014/004406.

* cited by examiner

ULTRASONIC FLAW DETECTOR AND METHOD OF OPERATING ULTRASONIC FLAW DETECTOR

TECHNICAL FIELD

The present invention relates to an ultrasonic flaw detector and a method of operating the ultrasonic flaw detector. The present invention particularly relates to an ultrasonic flaw detector that performs inspection of a composite component and a method of operating the ultrasonic flaw detector.

BACKGROUND ART

Defect inspection of a composite component is performed with use of an ultrasonic flaw detector by a transmission method or a reflection method. The inspection by the transmission method is performed in the following manner: receive an ultrasonic wave that has been transmitted through a composite member; and determine based on the energy of the received ultrasonic wave whether or not the composite member has a defect. On the other hand, the inspection by the reflection method is performed in the following manner: receive an ultrasonic wave that has reflected on a composite member; and determine based on the energy of the received ultrasonic wave whether or not the composite member has a defect.

There is a known inspection apparatus that performs inspection in a manner to switch between the transmission method and the reflection method (see Patent Literature 1, for example). In the inspection apparatus disclosed in Patent Literature 1, a pair of probes is disposed such that the probes are positioned at both sides of a composite member in a manner to face each other. The inspection apparatus includes switching means that switches between transmission-type inspection in which both of the pair of probes are utilized and reflection-type inspection in which only one of the probes is utilized. The inspection apparatus disclosed in Patent Literature 1 includes a feeder that feeds composite members having the same shape (inspection objects; brake pads) to an inspection unit.

At the time of performing defect inspection of a composite component, it is necessary to perform calibration using a calibration test piece (a standard sample) before and after the defect inspection in order to verify the soundness of the ultrasonic flaw detector. In order to perform such calibration of the ultrasonic flaw detector, there is a known ultrasonic flaw detector that makes it possible to perform calibration and verification of probes on an off line under the same conditions as those of an actual line (see Patent Literature 2, for example). The ultrasonic flaw detector disclosed in Patent Literature 2 includes: a plurality of calibration test pieces that are arranged in the direction of a conveyer line and on each of which an artificial flaw is formed; and a truck that is fitted with a plurality of probe heads and movable in the width direction of a steel plate and that moves the probe heads over the calibration test pieces.

CITATION LIST

Patent Literature

PTL 1: Japanese Laid-Open Patent Application Publication No. 2002-31623

PTL 2: Japanese Laid-Open Patent Application Publication No. H11-326296

SUMMARY OF INVENTION

Technical Problem

However, the ultrasonic flaw detectors disclosed in Patent Literatures 1 and 2 are intended to perform inspection of inspection objects having the same shape (a simple plate shape), and are not intended to perform inspection of inspection objects having different shapes (complex shapes). Thus, there is still room for improvements for ultrasonic flaw detectors.

The present invention solves the above-described conventional problems. An object of the present invention is to provide an ultrasonic flaw detector capable of reducing a work time when performing flaw detection inspection of an inspection object having a complex shape by use of at least two types of flaw detection heads, and to provide a method of operating the ultrasonic flaw detector.

Solution to Problem

In order to solve the above-described conventional problems, an ultrasonic flaw detector according to the present invention includes: a first flaw detection head including a probe; a second flaw detection head including a probe; a moving mechanism that causes the first flaw detection head and the second flaw detection head to perform scanning; a calibration area in which a calibration standard sample is disposed; a flaw detection area in which an inspection object is disposed; and a controller that performs a first calibration process or a second calibration process, the first calibration process being a process of causing the first flaw detection head to scan the calibration standard sample to perform calibration using the calibration standard sample, the second calibration process being a process of causing the second flaw detection head to scan the calibration standard sample to perform calibration using the calibration standard sample when performing a first flaw detection process of performing ultrasonic flaw detection inspection of the inspection object by the first flaw detection head.

This makes it possible to reduce the work time even in the case of performing flaw detection inspection of an inspection object having a complex shape.

A method of operating an ultrasonic flaw detector according to the present invention includes: performing a first calibration process or a second calibration process, the first calibration process being a process of causing a first flaw detection head to scan a calibration standard sample to perform calibration using the calibration standard sample, the second calibration process being a process of causing a second flaw detection head to scan the calibration standard sample to perform calibration using the calibration standard sample when performing a first flaw detection process of performing ultrasonic flaw detection inspection of an inspection object by the first flaw detection head.

This makes it possible to reduce the work time even in the case of inspecting an inspection object having a complex shape.

Advantageous Effects of Invention

The ultrasonic flaw detector and the method of operating an ultrasonic flaw detector according to the present invention make it possible to reduce the work time even in the case of inspecting an inspection object having a complex shape.

DESCRIPTION OF EMBODIMENTS

Figure 1:
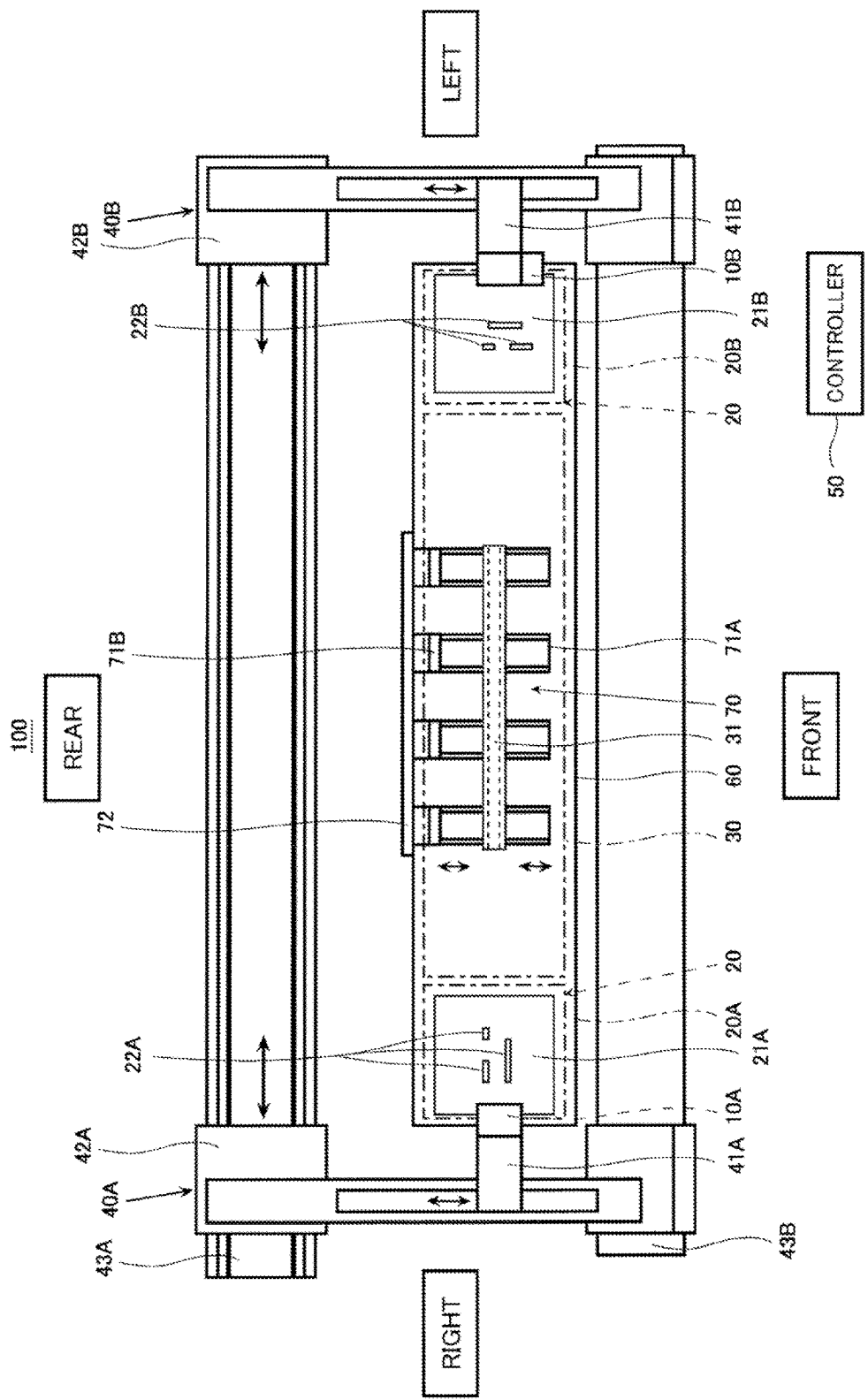
FIG. 1 is a schematic diagram showing a schematic configuration of an ultrasonic flaw detector according to Embodiment 1.

Hereinafter, preferred embodiments of the present invention are described with reference to the drawings. In the drawings, the same or corresponding components are denoted by the same reference signs, and repeating the same descriptions is avoided. In the drawings, only the components necessary for describing the present invention may be shown, and the other components may be omitted. Further, the present invention is not limited to the embodiments described below.

Embodiment 1

An ultrasonic flaw detector according to Embodiment 1 includes: a first flaw detection head including a probe; a second flaw detection head including a probe; a moving mechanism that causes the first flaw detection head and the second flaw detection head to perform scanning; a calibration area in which a calibration standard sample is disposed; a flaw detection area in which an inspection object is disposed; and a controller that performs a first calibration process or a second calibration process, the first calibration process being a process of causing the first flaw detection head to scan the calibration standard sample to perform calibration using the calibration standard sample, the second calibration process being a process of causing the second flaw detection head to scan the calibration standard sample to perform calibration using the calibration standard sample when performing a first flaw detection process of performing ultrasonic flaw detection inspection of the inspection object by the first flaw detection head.

According to the above configuration, even in the case of inspecting an inspection object having a complex shape, the work time can be reduced.

In the ultrasonic flaw detector according to Embodiment 1, one of the first flaw detection head and the second flaw detection head may be configured to perform ultrasonic flaw detection of a flat portion of the inspection object, and the other flaw detection head may be configured to perform ultrasonic flaw detection of a curved portion of the inspection object.

In the ultrasonic flaw detector according to Embodiment 1, the calibration area may include a first calibration area and a second calibration area, in each of which the calibration standard sample is disposed; the flaw detection area may be formed to be interposed between the first calibration area and the second calibration area; the first flaw detection head may be configured to perform calibration using the calibration standard sample disposed in the first calibration area; and the second flaw detection head may be configured to perform calibration using the calibration standard sample disposed in the second calibration area.

Hereinafter, one example of the ultrasonic flaw detector according to Embodiment 1 is described in detail with reference to the drawings.

[Configuration of Ultrasonic Flaw Detector]

Figure 2:
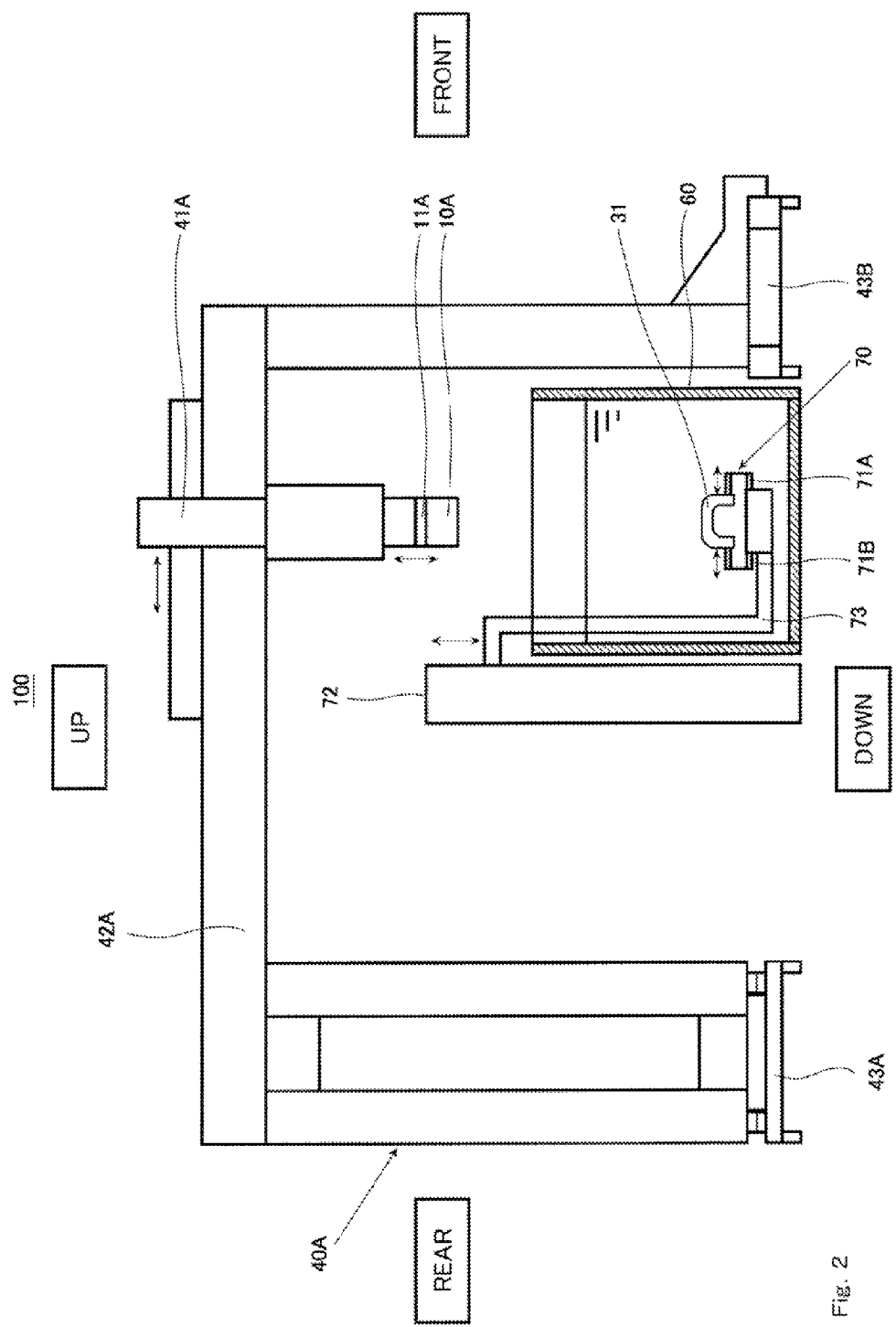
FIG. 2 is a schematic diagram showing a schematic configuration of the ultrasonic flaw detector according to Embodiment 1.

FIG. 1 and FIG. 2 are schematic diagrams each showing a schematic configuration of the ultrasonic flaw detector according to Embodiment 1. FIG. 1 is a schematic diagram showing a top view of the ultrasonic flaw detector, and FIG. 2 is a schematic diagram showing a front view of the ultrasonic flaw detector. It should be noted that, in FIG. 1, the front-rear direction and the right-left direction of the ultrasonic flaw detector are the front-rear direction and the right-left direction shown in FIG. 1. Similarly, in FIG. 2, the up-down direction and the right-left direction of the ultrasonic flaw detector are the up-down direction and the right-left direction shown in FIG. 2. FIG. 2 shows the internal configuration of a container for the purpose of showing the shape of each device provided inside the container.

As shown in FIG. 1 and FIG. 2, an ultrasonic flaw detector 100 according to Embodiment 1 includes: a first flaw detection head 10A and a second flaw detection head 10B, each of which includes a sensor (a probe) that inspects an inspection object 31; a first moving mechanism 40A; a second moving mechanism 40B; a controller 50; and a container 60.

The first moving mechanism 40A and the second moving mechanism 40B are disposed at both ends of the ultrasonic flaw detector 100 in the right-left direction, respectively, such that the first moving mechanism 40A and the second moving mechanism 40B face each other with the container 60 positioned in between them. The first moving mechanism 40A and the second moving mechanism 40B are configured to move in the right-left direction along a pair of guide members 43A and 43B.

The guide member 43A and the guide member 43B are formed to extend in the longitudinal direction of the container 60 (i.e., in the right-left direction). The guide member 43A and the guide member 43B are disposed such that, when seen in the up-down direction of the ultrasonic flaw detector 100, the guide member 43A and the guide member 43B are parallel to each other with the container 60 positioned in between them.

It should be noted that the controller 50 is disposed at a suitable position outside the container 60.

The first moving mechanism 40A is configured to cause the first flaw detection head 10A to scan the inspection object 31, and the second moving mechanism 40B is configured to cause the second flaw detection head 10B to scan the inspection object 31. It should be noted that the first moving mechanism 40A and the second moving mechanism 40B form a moving mechanism of the present invention.

Each of the first flaw detection head 10A and the second flaw detection head 10B includes a probe. The first flaw detection head 10A and the second flaw detection head 10B are configured to be able to scan different parts (portions), respectively, of the inspection object 31, which is to be inspected. It should be noted that the probes of the first flaw detection head 10A and the second flaw detection head 10B herein are each configured to transmit an ultrasonic wave and receive the ultrasonic wave that has reflected on the inspection object 31.

The container 60 is formed in the shape of a rectangular parallelepiped. The upper part of the container 60 is open. Water is stored in the internal space of the container 60. A calibration standard sample 21A, a calibration standard sample 21B, and the inspection object 31 are disposed in the internal space of the container 60. Although Embodiment 1 adopts a configuration in which water is stored in the internal space of the container 60, the configuration is not thus limited. Alternatively, a configuration in which no water is stored in the internal space of the container 60, i.e., a configuration in which the internal space of the container 60 is filled with air, may be adopted.

The calibration standard sample 21A and the calibration standard sample 21B are disposed at both ends in the internal space of the container 60 in the right-left direction, respectively. Artificial defects 22A necessary for performing calibration of the first flaw detection head 10A are formed in the calibration standard sample 21A, and artificial defects 22B necessary for performing calibration of the second flaw detection head 10B are formed in the calibration standard sample 21B. It should be noted that artificial defects necessary for performing calibration of all types of flaw detection heads may be formed in the calibration standard sample 21A and the calibration standard sample 21B.

A space in which the calibration standard sample 21A is disposed forms a first calibration area 20A, and a space in which the calibration standard sample 21B is disposed forms a second calibration area 20B. The first calibration area 20A and the second calibration area 20B form calibration areas 20.

A flaw detection area 30 is formed between the first calibration area 20A and the second calibration area 20B. The inspection object (a composite component) 31 is disposed in the flaw detection area 30. The inspection object 31 herein is long in the right-left direction and has a U-shaped cross section. The inspection object 31 is disposed such that its curved portion is positioned upward (see FIG. 2).

It should be noted that, in Embodiment 1, the inspection object 31 may be, for example, an aircraft component that is formed by composite members. The cross-sectional shape of the inspection object 31 is not limited to a U-shape, but may be any shape among various shapes including a T-shape, I-shape, L-shape, etc.

The ultrasonic flaw detector 100 includes a retaining mechanism 70 for retaining the inspection object 31 during flaw detection. The retaining mechanism 70 includes pairs of arm members 71A and 71B (in this example, four pairs of arm members 71A and 71B). The arm members 71A and 71B are disposed in the internal space of the container 60. The retaining mechanism 70 retains the inspection object 31 by sandwiching portions of the inspection object 31 with use of the arm members 71A and 71B, the portions being not subjected to the scanning by the first flaw detection head 10A and the second flaw detection head 10B (in this example, the portions are both ends of the inspection object 31 (specifically, both ends in the front-rear direction (width direction)).

Next, devices forming the ultrasonic flaw detector 100 according to Embodiment 1 are further described in detail with reference to FIG. 1 and FIG. 2.

[Configuration of Moving Mechanism]

The first moving mechanism 40A includes a first moving part 41A and a first gantry part 42A, and is disposed at the right-side end of the ultrasonic flaw detector 100. The first moving mechanism 40A includes known actuators such as motors, gears, pistons, or cylinders. The first moving mechanism 40A is configured to cause, by use of the actuators, the first flaw detection head 10A to move and/or rotate in the front-rear, right-left, and up-down directions. That is, the first moving mechanism 40A is configured to cause the first flaw detection head 10A to move triaxially and/or rotate triaxially. It should be noted that the actuators of the first moving mechanism 40A may be in any form, so long as the actuators can cause the first flaw detection head 10A to move and/or rotate in the front-rear, right-left, and up-down directions.

The first gantry part 42A is formed to be arch-shaped such that the first gantry part 42A straddles over the container 60 when seen in the right-left direction. Specifically, the first gantry part 42A includes a pair of leg portions provided upright at the right and left sides of the container 60 and a bridging portion connecting between the upper ends of the leg portions. The base ends of the pair of leg portions of the first gantry part 42A are in contact with the upper ends of the guide members 43A and 43B, respectively. Actuators, such as motors, are provided at the base ends of the leg portions of the first gantry part 42A (not shown) so that the gantry part 42A can move along the guide members 43A and 43B.

The first moving mechanism 40A can move linearly in the right-left direction by moving along the guide members 43A and 43B, thereby moving the first flaw detection head 10A in the right-left direction. It should be noted that one of or both the guide member 43A and the guide member 43B may be eliminated, so long as the first moving mechanism 40A can move linearly in the right-left direction (i.e., in a non-serpentine manner).

The bridging portion of the first gantry part 42A is provided with: the first moving part 41A extending downward; and an actuator such as a motor (not shown) that allows the first moving part 41A to move in the front-rear direction. The first moving part 41A is provided with an actuator such as a motor that allows the first flaw detection head 10A to advance or retreat in the up-down direction. Accordingly, the first flaw detection head 10A can move in the front-rear or up-down direction.

Similar to the first moving mechanism 40A, the second moving mechanism 40B includes a second moving part 41B and a second gantry part 42B, and is disposed at the left-side end of the ultrasonic flaw detector 100. Since the second moving mechanism 40B is configured in the same manner as the first moving mechanism 40A, a detailed description of the second moving mechanism 40B is omitted.

[Configuration of Flaw Detection Head]

The first flaw detection head 10A is mounted to the first moving part 41A of the first moving mechanism 40A via a mounting portion 11A (see FIG. 2). Similarly, the second flaw detection head 10B is mounted to the second moving part 41B of the second moving mechanism 40B via a mounting portion (not shown). It should be noted that the first flaw detection head 10A can be mounted to the second moving part 41B of the second moving mechanism 40B, and the second flaw detection head 10B can be mounted to the first moving part 41A of the first moving mechanism 40A via the mounting portion 11A.

The first flaw detection head 10A is configured to perform ultrasonic flaw detection on flat portions of the inspection object 31. Specifically, the first flaw detection head 10A is configured to perform ultrasonic flaw detection on flat-shaped portions of the inspection object 31, such as the inner bottom surface, the outer bottom surface, and the side surfaces of the inspection object 31.

The second flaw detection head 10B is configured to perform ultrasonic flaw detection on curved portions of the inspection object 31. Specifically, the second flaw detection head 10B is configured to perform ultrasonic flaw detection on bent portions of the inspection object 31.

It should be noted that the first flaw detection head 10A may include a plurality of types of flaw detection heads, each of which has a different width dimension (the dimension in the right-left direction) and/or a different height dimension (the dimension in the up-down direction). Specifically, the first flaw detection head 10A may include a flaw detection head with a wide flaw detection range and a flaw detection head with a narrow flaw detection range.

For example, in a case where the width dimension of a flat portion of the inspection object 31 is great, if a flaw detection head with a small width dimension (i.e., one with a narrow flaw detection range) is used, then it is necessary for the flaw detection head to scan the inspection object 31 many times. In this respect, if a flaw detection head with a great width dimension (i.e., one with a wide flaw detection range) is used, the number of times the flaw detection head scans the inspection object 31 can be reduced.

For example, in a case where the inspection object 31 has a U-shaped cross section as shown in FIG. 2, in order to scan a flat portion of the inner surface of the inspection object 31, it is necessary to use a flaw detection head with a small width dimension (i.e., one with a narrow flaw detection range). Otherwise, the distance between the inner surface of the inspection object 31 and the probe will be great, which may result in imprecise inspection.

In view of the above, a flaw detection head of a wide flaw detection range type and a flaw detection head of a narrow flaw detection range type may be mounted to the first moving part 41A of the first moving mechanism 40A so that the type of the flaw detection head to use can be changed as necessary in accordance with the width dimension or the like of the inspection object 31.

The second flaw detection head 10B may include a flaw detection head that scans the inner surface side of the inspection object 31 and a flaw detection head that scans the outer surface side of the inspection object 31. In this case, these two types of flaw detection heads may be mounted to the second moving part 41B of the second moving mechanism 40B, and the flaw detection head to use may be selectively switched between the case of scanning the inner surface of the inspection object 31 and the case of scanning the outer surface of the inspection object 31.

[Configuration of Retaining Mechanism]

The retaining mechanism 70 includes: the pairs of arm members 71A and 71B; a container 72, which accommodates actuators such as motors (not shown); and a connection part 73, which connects the arm members 71A and 71B and the container 72. The actuators disposed inside the container 72 are configured to move the connection part 73 in the up-down direction and also drive a belt mechanism and so forth described below.

The arm members 71A and the arm members 71B herein are each formed to be U-shaped, and are disposed such that the arm members 71A and the arm members 71B face each other with the container 72 positioned in between them. To be more specific, the left-side arm members 71A are each formed to have a U shape that is open to the right side, and the right-side arm members 71B are each formed to have a U shape that is open to the left side.

The arm members 71A and the arm members 71B are arranged such that their openings face each other. One of the distal ends (the lower end) of each of the arm members 71A and the arm members 71B is connected to one end of the connection part 73. The other end of the connection part 73 is connected to the actuators inside the container 72.

The connection part 73 is sealed up by suitable means, for example, by use of an O-ring so that water will not enter the inside. Members that allow the arm members 71A and 71B to advance or retreat (i.e., to move closer to each other or move away from each other) in the front-rear direction, such as a belt mechanism, rack, pinion, etc., are disposed inside the connection part 73.

Accordingly, by bringing the other distal end (the upper end) of each of the arm members 71A and the arm members 71B into contact with the inspection object 31, the inspection object 31 can be retained. By moving the other distal of each of the arm members 71A and the arm members 71B away from the inspection object 31, the inspection object 31 can be released from the retained state.

It should be noted that the actuators of the retaining mechanism 70 may be in any form, so long as the actuators can cause the arm members 71A and the arm members 71B to advance or retreat in the front-rear and up-down directions. In addition, the actuators of the retaining mechanism 70 may be configured to cause the arm members 71A and the arm members 71B to advance or retreat in the right-left direction. Further, a component receiving member (a supporting member) for suppressing the inspection object 31 from bending may be disposed on the upper surface of the container 72 of the retaining mechanism 70.

[Configuration of Controller]

The controller 50 is configured to control components (devices) forming the ultrasonic flaw detector 100. The controller 50 includes: an arithmetic processing unit, such as a microprocessor or a CPU; a storage unit; and an input unit. Through the loading and execution, by the arithmetic processing unit, of a predetermined control program stored in the storage unit, the controller 50 performs various controls of the ultrasonic flaw detector 100.

The storage unit is configured to store various data in a retrievable manner. Examples of the storage unit include known storage devices, such as memories and hard disks. The input unit is configured to input, for example, various parameters relating to the control of each component of the ultrasonic flaw detector 100 or other data to the arithmetic processing unit. A known input device, such as a keyboard, a touch panel, a group of push button switches, or the like, serves as the input unit.

It should be noted that the controller 50 may be configured not only as a single controller, but as a group of multiple controllers that operate in cooperation with each other to control the ultrasonic flaw detector 100. Moreover, the controller 50 may be configured as a microcontroller. Furthermore, the controller 50 may be configured as an MPU, PLC (Programmable Logic Controller), logic circuit, or the like.

While the first moving mechanism 40A is moving inside the flaw detection area 30, the controller 50 controls the second moving mechanism 40B so that the second moving mechanism 40B will not move into the flaw detection area 30. While the second moving mechanism 40B is moving inside the flaw detection area 30, the controller 50 controls the first moving mechanism 40A so that the first moving mechanism 40A will not move into the flaw detection area 30.

[Operations (Operation Method) of Ultrasonic Flaw Detector]

Next, operations (operation method) of the ultrasonic flaw detector 100 according to Embodiment 1 are described with reference to FIG. 1 to FIG. 3.

Figure 3:
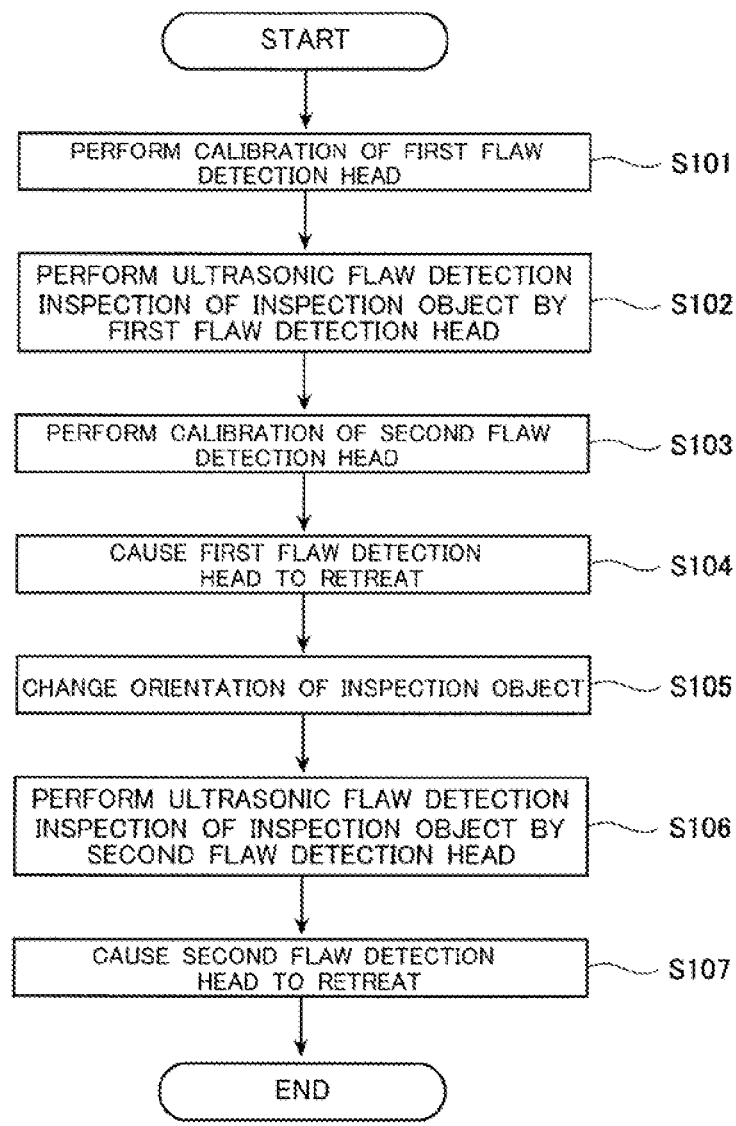
FIG. 3 is a flowchart showing one example of operations of the ultrasonic flaw detector according to Embodiment 1.

FIG. 3 is a flowchart showing one example of operations of the ultrasonic flaw detector according to Embodiment 1.

First, it is assumed that, as shown in FIG. 1, the first moving mechanism 40A of the ultrasonic flaw detector 100 is positioned at the left-side end of the guide members 43A and 43B (hereinafter, this position is referred to as the initial position of the first moving mechanism 40A), and the second moving mechanism 40B is positioned at the right-side end of the guide members 43A and 43B (hereinafter, this position is referred to as the initial position of the second moving mechanism 40B). It is also assumed that the inspection object 31 has been conveyed to the flaw detection area 30 by suitable means, and is in the state of being retained by the retaining mechanism 70.

In this state, the controller 50 performs operations of the ultrasonic flaw detector 100 in a manner described below.

As shown in FIG. 3, the controller 50 performs calibration of the first flaw detection head 10A (a first calibration process) (step S101). Specifically, the controller 50 operates the first moving mechanism 40A such that the first flaw detection head 10A scans the upper surface of the calibration standard sample 21A.

At the time, the controller 50 operates the first moving mechanism 40A such that the distance between the first flaw detection head 10A and the upper surface of the calibration standard sample 21A is a predetermined distance. The controller 50 also operates the first moving mechanism 40A such that the first flaw detection head 10A passes above the artificial defects 22A formed in the calibration standard sample 21A. Then, the controller 50 confirms that the first flaw detection head 10A detects the artificial defects 22A, and also confirms that the first flaw detection head 10A does not detect any defects from portions (of the calibration standard sample 21A) in which no artificial defect 22A is formed.

It should be noted that in a case where it is confirmed that there is an abnormality in the first flaw detection head 10A, for example, a case where the first flaw detection head 10A does not detect the artificial defects 22A, a necessary step is taken to eliminate the abnormality. Then, after confirming that the first flaw detection head 10A is in a normal state, the controller 50 performs step S102, which is the next step.

In step S102, the controller 50 performs ultrasonic flaw detection inspection of the inspection object 31 by the first flaw detection head 10A (a first flaw detection process). Specifically, the first moving mechanism 40A moves to the right side such that the first flaw detection head 10A scans the upper surface (front surface) of the inspection object 31. At the time, the first moving mechanism 40A operates such that the distance between the first flaw detection head 10A and the upper surface of the inspection object 31 is a predetermined distance.

It should be noted that the ultrasonic flaw detection inspection of the inspection object 31 by the first flaw detection head 10A may be performed when the first flaw detection head 10A moves from the left-side end toward the right-side end of the inspection object 31 and/or when the first flaw detection head 10A moves from the right-side end toward the left-side end of the inspection object 31.

The controller 50 performs calibration of the second flaw detection head 10B (a second calibration process) while the ultrasonic flaw detection inspection of the inspection object 31 by the first flaw detection head 10A is being performed (step S103). Specifically, the controller 50 operates the second moving mechanism 40B such that the second flaw detection head 10B scans the upper surface of the calibration standard sample 21B.

At the time, the controller 50 operates the second moving mechanism 40B such that the distance between the second flaw detection head 10B and the upper surface of the calibration standard sample 21B is a predetermined distance. The controller 50 also operates the second moving mechanism 40B such that the second flaw detection head 10B passes above the artificial defects 22B formed in the calibration standard sample 21B. Then, the controller 50 confirms that the second flaw detection head 10B detects the artificial defects 22B, and also confirms that the second flaw detection head 10B does not detect any defects from portions (of the calibration standard sample 21B) in which no artificial defect 22B is formed.

It should be noted that in a case where it is confirmed that there is an abnormality in the second flaw detection head 10B, for example, a case where the second flaw detection head 10B does not detect the artificial defects 22B, a necessary step is taken to eliminate the abnormality. Then, after confirming that the second flaw detection head 10B is in a normal state, the controller 50 performs step S104, which is the next step.

In step S104, the controller 50 causes the first flaw detection head 10A to retreat. Specifically, the controller 50 operates the first moving mechanism 40A to move the first flaw detection head 10A to the initial position of the first moving mechanism 40A.

Next, the controller 50 causes an orientation changing mechanism 80 to change the orientation of the inspection object 31 (step S105). Specifically, in a state where an operator is holding the inspection object 31, the controller 50 causes the retaining mechanism 70 to release the inspection object 31 from the retained state. Thereafter, the operator changes the orientation of the inspection object 31. Then, the controller 50 causes the retaining mechanism 70 to retain the inspection object 31 again.

Subsequently, the controller 50 performs ultrasonic flaw detection inspection of the inspection object 31 by the second flaw detection head 10B (a second flaw detection process) (step S106). Specifically, the second moving mechanism 40B moves to the left side such that the second flaw detection head 10B scans the upper surface (front surface) of the inspection object 31. At the time, the second moving mechanism 40B operates such that the distance between the second flaw detection head 10B and the upper surface of the inspection object 31 is a predetermined distance.

It should be noted that the ultrasonic flaw detection inspection of the inspection object 31 by the second flaw detection head 10B may be performed when the second flaw detection head 10B moves from the right-side end toward the left-side end of the inspection object 31 and/or when the second flaw detection head 10B moves from the left-side end toward the right-side end of the inspection object 31.

Next, the controller 50 causes the second flaw detection head 10B to retreat (step S107). Specifically, the controller 50 operates the second moving mechanism 40B to move the second flaw detection head 10B to the initial position of the second moving mechanism 40B.

Then, the controller 50 performs orientation change of the inspection object 31 and ultrasonic flaw detection inspection of the inspection object 31 by the first flaw detection head 10A and/or the second flaw detection head 10B until flaw detection inspection is performed on all the portions (i.e., all the side surfaces) of the inspection object 31. After the flaw detection inspection is performed on all the portions (i.e., all the side surfaces) of the inspection object 31, the controller 50 performs calibration of the first flaw detection head 10A and the second flaw detection head 10B, and thus the first flaw detection head 10A and the second flaw detection head 10B are confirmed to be in a normal state before and after the flaw detection inspection of the inspection object 31.

It should be noted that, while the final flaw detection inspection of the inspection object 31 is being performed, the controller 50 may control the first moving mechanism 40A or the second moving mechanism 40B so as to perform calibration of the flaw detection head that is not performing the flaw detection inspection. In this manner, the time required for the calibration work can be reduced.

In the above-described manner, the ultrasonic flaw detector 100 according to Embodiment 1 performs the calibration of the first flaw detection head 10A and the second flaw detection head 10B and the ultrasonic flaw detection inspection of the inspection object 31.

[Functional Advantages of Ultrasonic Flaw Detector]

As described above, the ultrasonic flaw detector 100 according to Embodiment 1 includes at least two types of flaw detection heads, and performs calibration of the second flaw detection head 10B while performing flaw detection inspection of the inspection object 31 by the first flaw detection head 10A or while performing calibration of the first flaw detection head 10A. This makes it possible to reduce the work time of the flaw detection inspection of the inspection object 31.

Moreover, in the ultrasonic flaw detector 100 according to Embodiment 1, it is not necessary to replace the flaw detection head with one adapted to the shape of the inspection object 31 each time the portion to be inspected of the inspection object 31 is changed. For this reason, the replacement time of the flaw detection head can be eliminated.

Furthermore, in a case where such flaw detection head replacement is necessary, each time the flaw detection head is replaced, calibration of the flaw detection head needs to be performed before and after flaw detection inspection of the inspection object 31. However, since the ultrasonic flaw detector according to Embodiment 1 does not require the flaw detection head replacement, the number of times the calibration of the flaw detection head is performed can be reduced. As a result, the work time of the flaw detection inspection of the inspection object 31 can be reduced.

Although in Embodiment 1 the calibration of the second flaw detection head 10B is performed while the flaw detection inspection of the inspection object 31 by the first flaw detection head 10A is being performed, the timing of performing the calibration of the second flaw detection head 10B is not thus limited. For example, the calibration of the second flaw detection head 10B may be performed while the calibration of the first flaw detection head 10A is being performed.

Embodiment 2

An ultrasonic flaw detector according to Embodiment 2 further includes an orientation changing mechanism that changes an orientation of the inspection object. The controller performs the second calibration process of causing the second flaw detection head to scan the calibration standard sample to perform calibration using the calibration standard sample when performing one of the following processes: the first calibration process of causing the first flaw detection head to scan the calibration standard sample to perform calibration using the calibration standard sample; the first flaw detection process of performing ultrasonic flaw detection inspection of the inspection object by the first flaw detection head; and an orientation changing process of changing the orientation of the inspection object by the orientation changing mechanism.

In the ultrasonic flaw detector according to Embodiment 2, the controller may perform the first calibration process and the second calibration process when performing the orientation changing process.

According to this configuration, even in the case of inspecting an inspection object having a complex shape, the work time can be reduced.

The ultrasonic flaw detector according to Embodiment 2 may further include a retaining mechanism that retains the inspection object and an orientation changing mechanism that changes an orientation of the inspection object. The controller may be configured to cause the retaining mechanism to retain the inspection object when performing ultrasonic flaw detection inspection of the inspection object, and may be configured to release the inspection object from a state of being retained by the retaining mechanism when changing the orientation of the inspection object by the orientation changing mechanism.

In the ultrasonic flaw detector according to Embodiment 2, the retaining mechanism may include a pair of arm members, and may be configured to retain the inspection object by sandwiching, by the pair of arm members, both ends of the inspection object that are not subjected to the scanning.

In the ultrasonic flaw detector according to Embodiment 2, the orientation changing mechanism may be configured to change the orientation of the inspection object by gripping a portion of the inspection object, the portion being different from portions retained by the retaining mechanism, and rotating the inspection object.

Hereinafter, one example of the ultrasonic flaw detector according to Embodiment 2 is described in detail with reference to the drawings.

[Configuration of Ultrasonic Flaw Detector]

Figure 4:
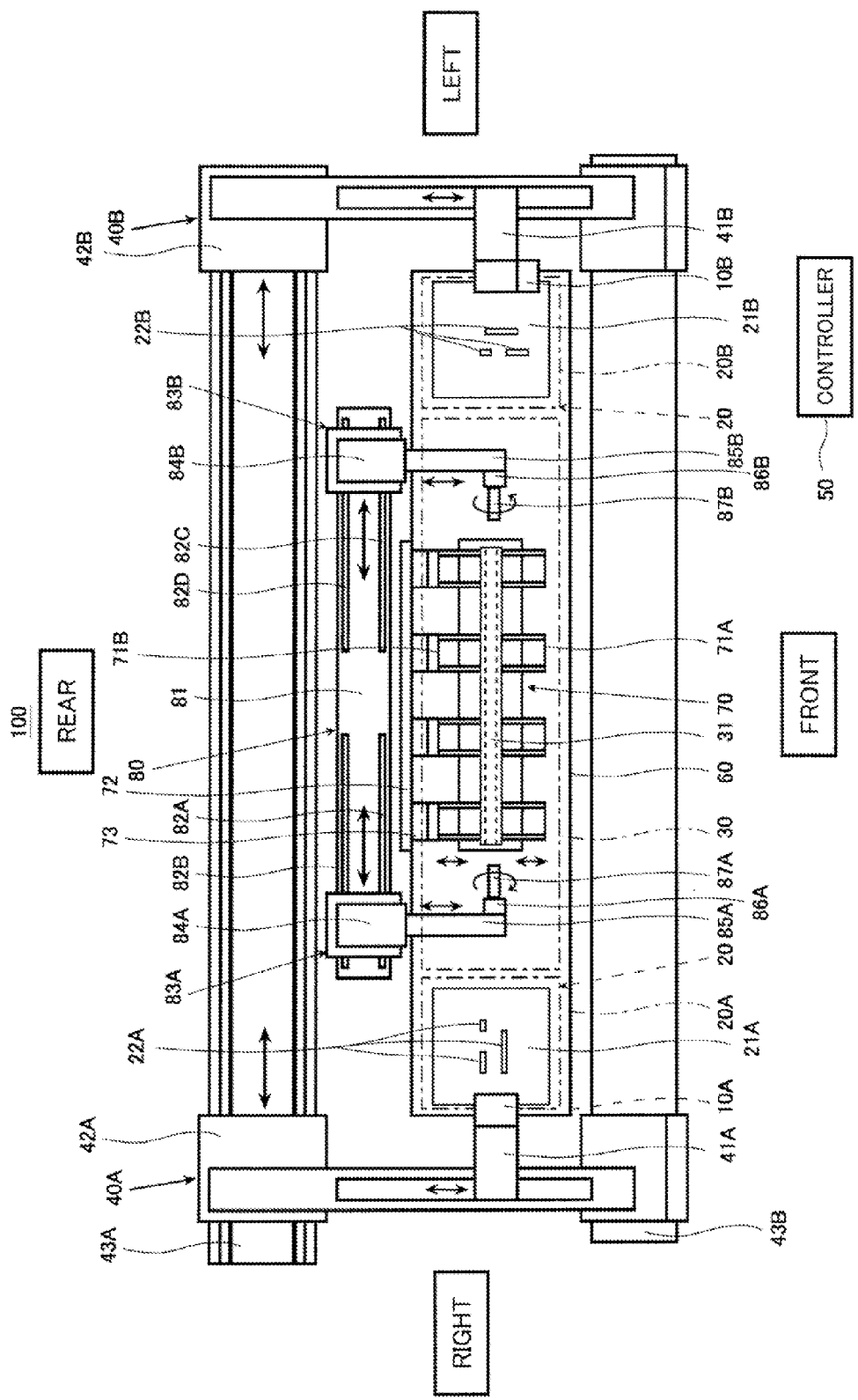
FIG. 4 is a schematic diagram showing a schematic configuration of an ultrasonic flaw detector according to Embodiment 2.
Figure 5:
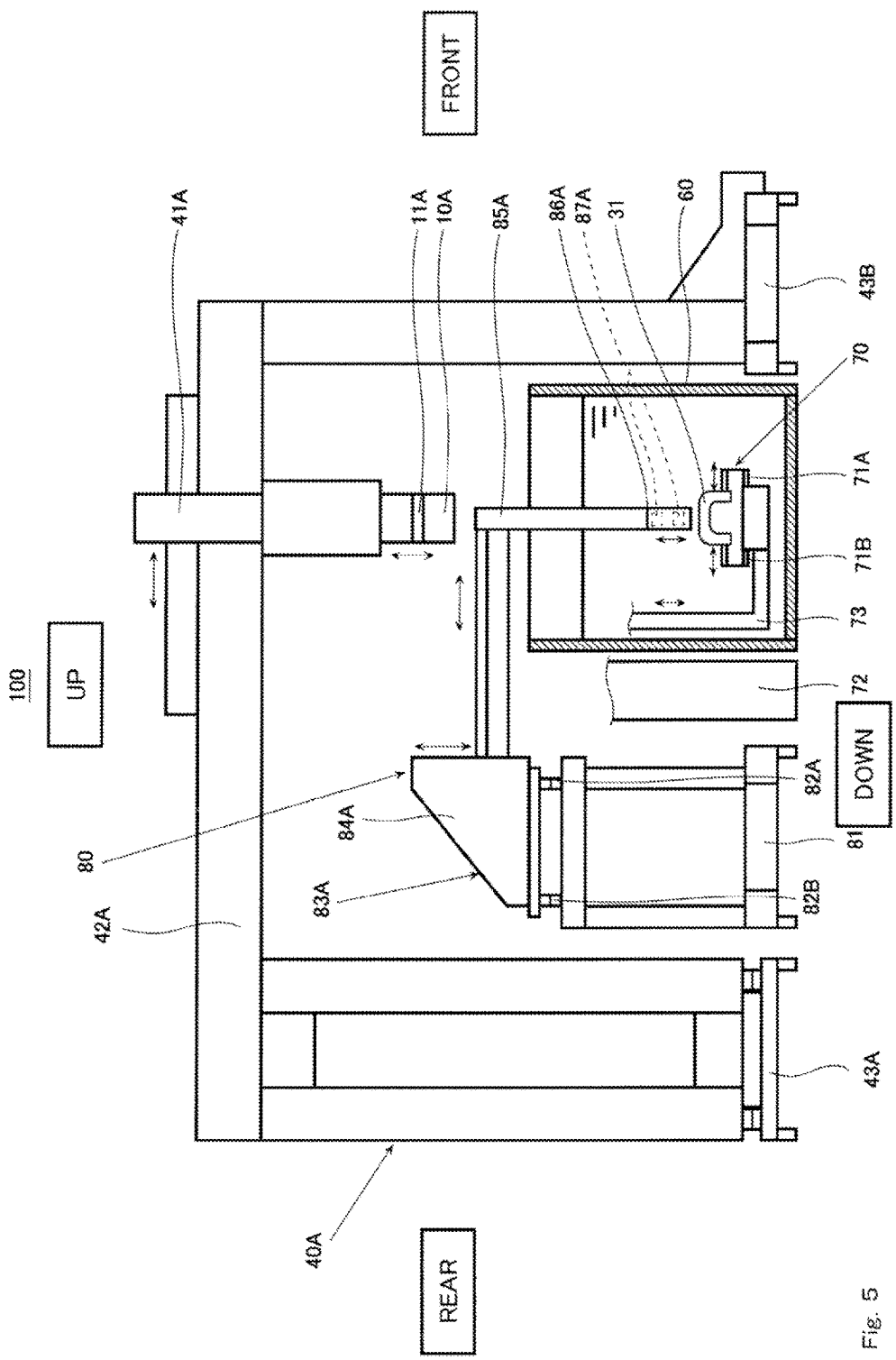
FIG. 5 is a schematic diagram showing a schematic configuration of the ultrasonic flaw detector according to Embodiment 2.

FIG. 4 and FIG. 5 are schematic diagrams each showing a schematic configuration of the ultrasonic flaw detector according to Embodiment 2. FIG. 4 is a schematic diagram showing a top view of the ultrasonic flaw detector, and FIG. 5 is a schematic diagram showing a front view of the ultrasonic flaw detector. It should be noted that, in FIG. 4, the front-rear direction and the right-left direction of the ultrasonic flaw detector are the front-rear direction and the right-left direction shown in FIG. 4. Similarly, in FIG. 5, the up-down direction and the right-left direction of the ultrasonic flaw detector are the up-down direction and the right-left direction shown in FIG. 5. FIG. 5 shows the internal configuration of a container for the purpose of showing the shape of each device provided inside the container. In FIG. 5, the container and connection part are partially omitted.

As shown in FIG. 4 and FIG. 5, the fundamental configuration of the ultrasonic flaw detector 100 according to Embodiment 2 is the same as that of the ultrasonic flaw detector 100 according to Embodiment 1. However, the ultrasonic flaw detector 100 according to Embodiment 2 is different from the ultrasonic flaw detector 100 according to Embodiment 1 in that the ultrasonic flaw detector 100 according to Embodiment 2 further includes the orientation changing mechanism 80. The orientation changing mechanism 80 is configured to change the orientation of the inspection object 31 while flaw detection of the inspection object 31 is not being performed. The orientation changing mechanism 80 is disposed at the rear of and outside of the container 60. It should be noted that part of the orientation changing mechanism 80 (e.g., an arm 85A described below) is positioned inside the container 60. Alternatively, the orientation changing mechanism 80 may be disposed inside the container 60 (at the inner bottom of the container 60).

The orientation changing mechanism 80 is configured to grip portions of the inspection object 31, the portions being not retained by the retaining mechanism 70 (in this example, the right-side and left-side ends of the inspection object 31), and rotate the inspection object 31, thereby changing the orientation of the inspection object 31. It should be noted that an angle by which the inspection object 31 is rotated may be set to any angle. For example, the inspection object 31 may be rotated clockwise by 45°, 90°, or 180°, or may be rotated counterclockwise by 450, 90°, or 180°, about an axis extending in the right-left direction (the longitudinal direction of the inspection object 31).

The orientation changing mechanism 80 includes a base 81, guides 82A, 82B, 82C, and 82D, a first driver 83A, and a second driver 83B. The base 81 is disposed between the container 60 and the guide member 43A, and serves as a support base that is long in the front-rear direction. The guides 82A to 82D are placed on the upper surface of the base 81. The guide 82A and the guide 82B are disposed at the right side of the base 81 and are arranged extending in the longitudinal direction of the container 60, such that the guide 82A and the guide 82B are parallel to each other. The guide 82C and the guide 82D are disposed at the left side of the base 81 and are arranged extending in the longitudinal direction of the container 60, such that the guide 82C and the guide 82D are parallel to each other.

The first driver 83A is disposed over the guide 82A and the guide 82B, and the second driver 83B is disposed over the guide 82C and the guide 82D. At the central portion of the upper surface of the base 81, the guides 82A and 82B and the guides 82C and 82D are spaced apart from each other.

This makes it possible to prevent the first driver 83A and the second driver 83B from contacting each other. It should be noted that, as described below, the controller 50 controls the first driver 83A and the second driver 83B so that they will not collide with each other. Therefore, it is not essential that the guides 82A and 82B and the guides 82C and 82D be spaced apart from each other at the aforementioned central portion.

The first driver 83A includes a truck 84A, the arm 85A, an attaching part 86A, a gripper 87A, an actuator such as a motor (not shown). The actuator is incorporated in the truck 84A. The truck 84A is configured to advance or retreat in the right-left direction by means of the actuator along the guide 82A and the guide 82B.

The arm 85A is formed to be L-shaped when seen in the right-left direction. Specifically, the arm 85A is connected to the actuator inside the truck 84A. The arm 85A is formed in a manner to extend forward from its one end, bend at a position above the container 60 to extend downward, and reach the other end. The attaching part 86A is attached to the other end of the arm 85A. The arm 85A is configured to move in the front-rear direction and/or the up-down direction by means of the actuator. The gripper 87A is attached to the attaching part 86A. The attaching part 86A is configured to rotate together with the gripper 87A about an axis extending in the right-left direction via suitable means.

The gripper 87A herein is formed by a pair of rod members. The pair of rod members is configured in such a manner that the rod members can come closer to or move away from each other so that the rod members can grip or release the inspection object 31. The gripper 87A is configured such that, when the gripper 87A rotates together with the attaching part 86A, the gripper 87A grips (sandwiches) the inspection object 31 with such force (pressure) that the inspection object 31 will not come off. It should be noted that the gripper 87A is not limited to the pair of rod members, but may be in any form, so long as the inspection object 31 will not come off during the rotation.

Similar to the first driver 83A, the second driver 83B includes a truck 84B, an arm 85B, an attaching part 86B, and an actuator such as a motor (not shown). Since the devices (components) forming the second driver 83B are configured in the same manner as the devices (components) forming the first driver 83A, the description of the configuration of the second driver 83B is omitted.

The controller 50 controls the first driver 83A and the second driver 83B so that they will not collide with each other. In addition, the controller 50 controls the first driver 83A and the second driver 83B so that they will not collide with each other while the first moving mechanism 40A or the second moving mechanism 40B is operating.

[Operations (Operation Method) of Ultrasonic Flaw Detector]

Next, operations (operation method) of the ultrasonic flaw detector 100 according to Embodiment 2 are described with reference to FIG. 4 to FIG. 7.

Figure 6:
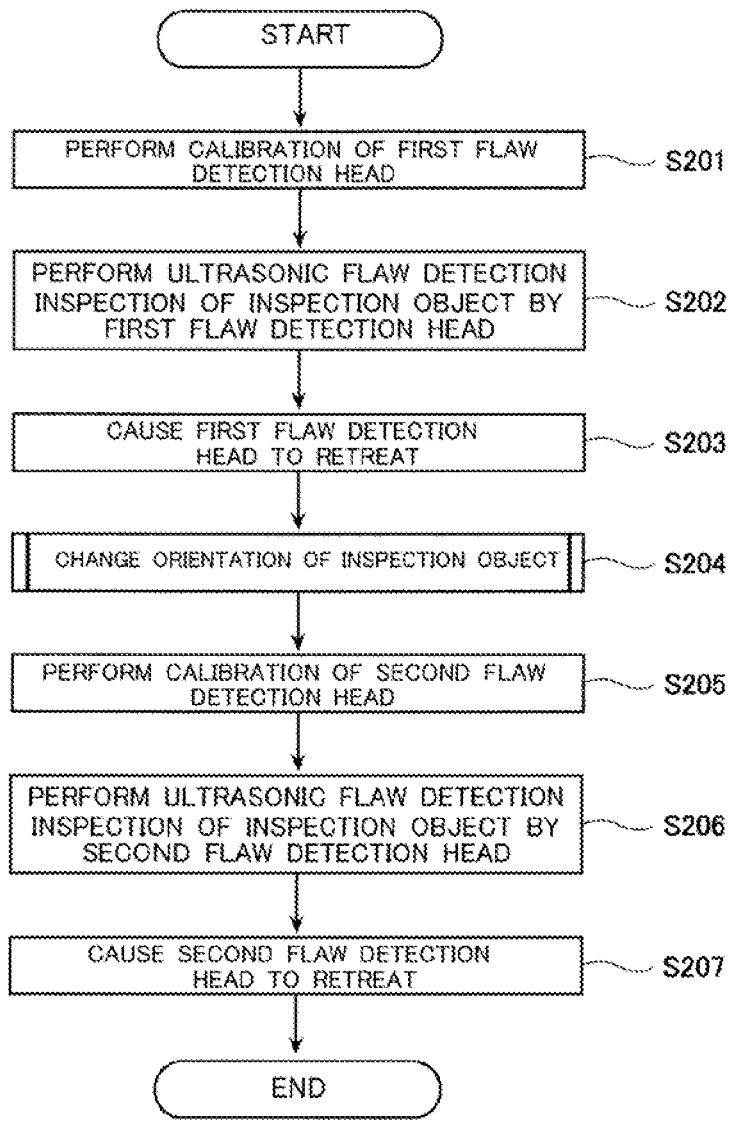
FIG. 6 is a flowchart showing one example of operations of the ultrasonic flaw detector according to Embodiment 2.
Figure 7:
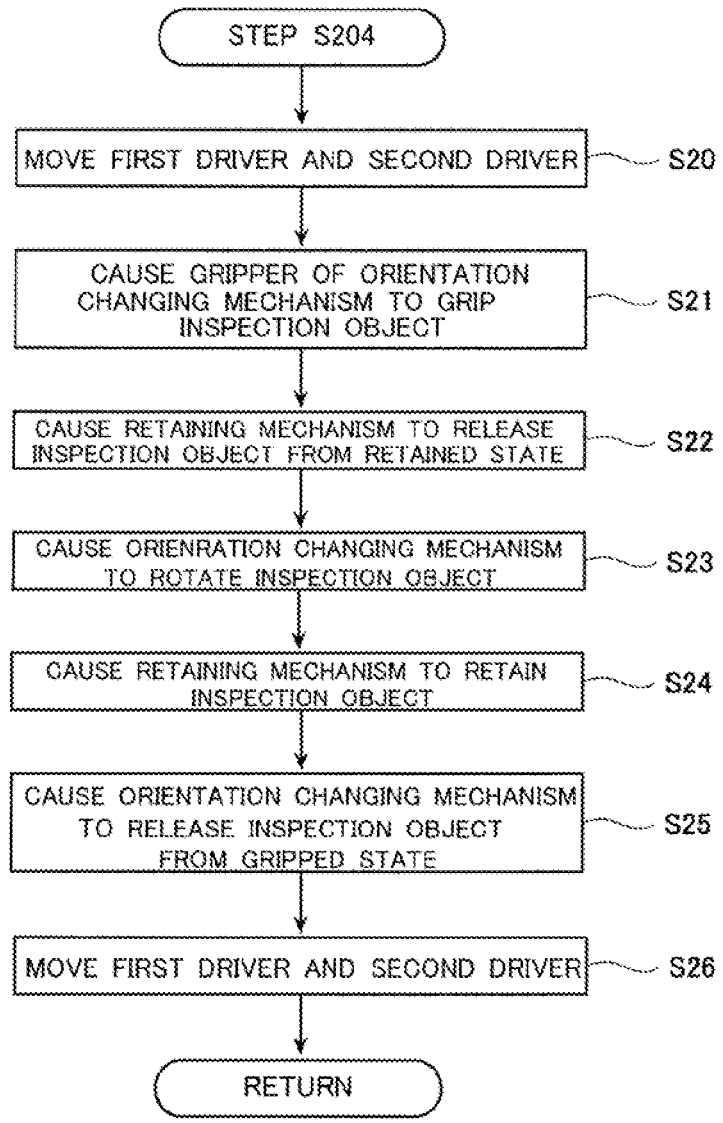
FIG. 7 is a flowchart showing step S204 of FIG. 6 in more detail.

FIG. 6 is a flowchart showing one example of operations of the ultrasonic flaw detector according to Embodiment 2. FIG. 7 is a flowchart showing step S204 of FIG. 6 in more detail.

First, similar to Embodiment 1, it is assumed that the first moving mechanism 40A of the ultrasonic flaw detector 100 is positioned at the initial position of the first moving mechanism 40A, and the second moving mechanism 40B is positioned at the initial position of the second moving mechanism 40B. It is also assumed that the inspection object 31 has been conveyed to the flaw detection area 30 by suitable means, and is in the state of being retained by the retaining mechanism 70. It is further assumed that the orientation changing mechanism 80 has retreated to a position (the initial position of the orientation changing mechanism 80) where the orientation changing mechanism 80 does not hinder movement of the first moving mechanism 40A (the first flaw detection head 10A) and the second moving mechanism 40B (the second flaw detection head 10B).

In this state, the controller 50 performs operations of the ultrasonic flaw detector 100 in a manner described below.

As shown in FIG. 6, the controller 50 performs calibration of the first flaw detection head 10A in the same manner as in Embodiment 1 (step S201). Then, the controller 50 performs ultrasonic flaw detection inspection of the inspection object 31 by the first flaw detection head 10A (step S202).

Next, the controller 50 causes the first flaw detection head 10A to retreat (step S203). Specifically, the controller 50 operates the first moving mechanism 40A to move the first flaw detection head 10A to the initial position of the first moving mechanism 40A.

Subsequently, the controller 50 causes the orientation changing mechanism 80 to change the orientation of the inspection object 31 (step S204). Hereinafter, the change of orientation of the inspection object 31 by the orientation changing mechanism 80 is described in detail with reference to FIG. 7.

It should be noted that if the operation of changing the orientation of the inspection object 31 by the orientation changing mechanism 80 is performable regardless of the position of the first flaw detection head 10A, then the operation of step S204 may be performed prior to the operation of step S203, or the operation of step S203 and the operation of step S204 may be performed at the same time.

As shown in FIG. 7, first, the controller 50 moves the first driver 83A to the right side such that the gripper 87A of the first driver 83A comes close to the left-side end of the inspection object 31, and moves the second driver 83B to the left side such that a gripper 87B of the second driver 83B comes close to the right-side end of the inspection object 31 (step S20).

Next, the controller 50 operates the first driver 83A and the second driver 83B such that the gripper 87A and the gripper 87B grip both ends of the inspection object 31 (step S21). Subsequently, the controller 50 causes the retaining mechanism 70 to release the inspection object 31 from the retained state (step S22). Specifically, the controller 50 operates the actuators of the retaining mechanism 70 to move the arm members 71A and the arm members 71B away from the inspection object 31.

Subsequently, the controller 50 drives the actuators of the orientation changing mechanism 80 to rotate the inspection object 31 by a predetermined angle about an axis whose axial direction is the longitudinal direction of the inspection object 31, and then stops the actuators of the orientation changing mechanism 80 (step S23). Thereafter, the controller 50 causes the retaining mechanism 70 to retain the inspection object 31 again (step S24). Specifically, the controller 50 operates the actuators of the retaining mechanism 70 such that the arm members 71A and the arm members 71B come into contact with the inspection object 31.

Next, the controller 50 causes the gripper 87A and the gripper 87B of the orientation changing mechanism 80 to release the inspection object 31 from the gripped state (step S25). Then, the controller 50 causes the first driver 83A and the second driver 83B to move to the initial position of the orientation changing mechanism 80 (step S26), and proceeds to step S205 of FIG. 6.

The controller 50 performs calibration of the second flaw detection head 10B while performing the operation of changing the orientation of the inspection object 31 by the orientation changing mechanism 80 (step S205). The controller 50 performs step S206 after confirming that the second flaw detection head 10B is in a normal state.

In step S206, the controller 50 performs ultrasonic flaw detection inspection of the inspection object 31 by the second flaw detection head 10B. Next, the controller 50 causes the second flaw detection head 10B to retreat (step S207). Then, the controller 50 performs orientation change of the inspection object 31 and ultrasonic flaw detection inspection of the inspection object 31 by the first flaw detection head 10A and/or the second flaw detection head 10B until flaw detection inspection is performed on all the portions (i.e., all the side surfaces) of the inspection object 31.

The ultrasonic flaw detector 100 according to Embodiment 2 with the above-described configuration performs calibration of the second flaw detection head 10B while the orientation changing mechanism 80 is changing the orientation of the inspection object 31. Accordingly, the ultrasonic flaw detector 100 according to Embodiment 2 provides the same functional advantages as those provided by the ultrasonic flaw detector 100 according to Embodiment 1.

Although in Embodiment 2 the flaw detection inspection of the inspection object 31 by the second flaw detection head 10B is performed after the flaw detection inspection of the inspection object 31 by the first flaw detection head 10A and the orientation change of the inspection object 31 have been performed, the present embodiment is not thus limited. For example, after the flaw detection inspection of the inspection object 31 by the first flaw detection head 10A and the orientation change of the inspection object 31 have been performed, flaw detection inspection of the inspection object 31 by the first flaw detection head 10A may be performed again. Similarly, after the flaw detection inspection of the inspection object 31 by the second flaw detection head 10B and the orientation change of the inspection object 31 have been performed, flaw detection inspection of the inspection object 31 by the second flaw detection head 10B may be performed again.

Although in Embodiment 2 the calibration of the second flaw detection head 10B is performed while the orientation changing mechanism 80 is changing the orientation of the inspection object 31, the present embodiment is not thus limited. For example, both the calibration of the first flaw detection head 10A and the calibration of the second flaw detection head 10B may be performed while the orientation changing mechanism 80 is changing the orientation of the inspection object 31. In this case, step S201 of FIG. 6 may be eliminated.

Embodiment 3

An ultrasonic flaw detector according to Embodiment 3 further includes a carry-in/out mechanism that carries the inspection object into or out of the flaw detection area. The controller performs the second calibration process of causing the second flaw detection head to scan the calibration standard sample to perform calibration using the calibration standard sample when performing one of the following processes: the first calibration process of causing the first flaw detection head to scan the calibration standard sample to perform calibration using the calibration standard sample; the first flaw detection process of performing ultrasonic flaw detection inspection of the inspection object by the first flaw detection head; and a carry-in/out process in which the carry-in/out mechanism carries the inspection object into or out of the flaw detection area.

In the ultrasonic flaw detector according to Embodiment 3, the controller may perform the first calibration process and the second calibration process when performing the carry-in/out process.

Hereinafter, one example of the ultrasonic flaw detector according to Embodiment 3 is described in detail with reference to the drawings.

[Configuration of Ultrasonic Flaw Detector]

Figure 8:
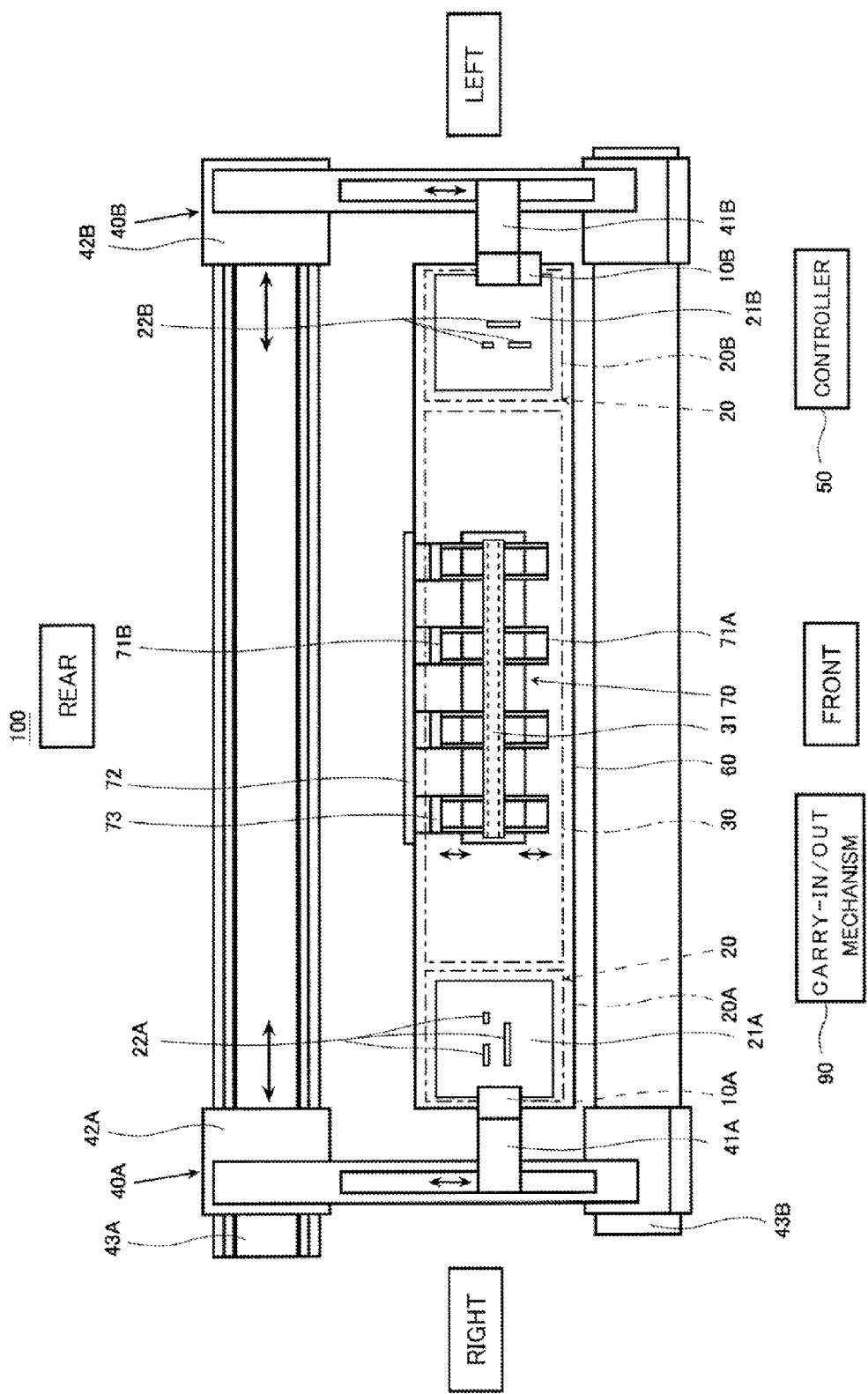
FIG. 8 is a schematic diagram showing a schematic configuration of an ultrasonic flaw detector according to Embodiment 3.

FIG. 8 is a schematic diagram showing a schematic configuration of the ultrasonic flaw detector according to Embodiment 3 and showing a top view of the ultrasonic flaw detector. It should be noted that, in FIG. 8, the front-rear direction and the right-left direction of the ultrasonic flaw detector are the front-rear direction and the right-left direction shown in FIG. 8.

As shown in FIG. 8, the fundamental configuration of the ultrasonic flaw detector 100 according to Embodiment 3 is the same as that of the ultrasonic flaw detector 100 according to Embodiment 1. However, the ultrasonic flaw detector 100 according to Embodiment 3 is different from the ultrasonic flaw detector 100 according to Embodiment 1 in that the ultrasonic flaw detector 100 according to Embodiment 3 further includes a carry-in/out mechanism 90. The carry-in/out mechanism 90 may be in any form, so long as the carry-in/out mechanism 90 can carry the inspection object 31 into and out of the ultrasonic flaw detector 100. For example, known equipment such as a belt conveyor, articulated robot, crane, suspended rails, etc., can be used as the carry-in/out mechanism 90. It should be noted that the carry-in/out mechanism 90 is controlled by the controller 50. Instead of the carry-in/out mechanism 90, an operator may carry in or carry out the inspection object 31. Further, the orientation changing mechanism 80 may include the carry-in/out mechanism 90.

[Operation (Operation Method) of Ultrasonic Flaw Detector]

Next, operations (operation method) of the ultrasonic flaw detector 100 according to Embodiment 3 are described with reference to FIG. 8 and FIG. 9.

Figure 9:
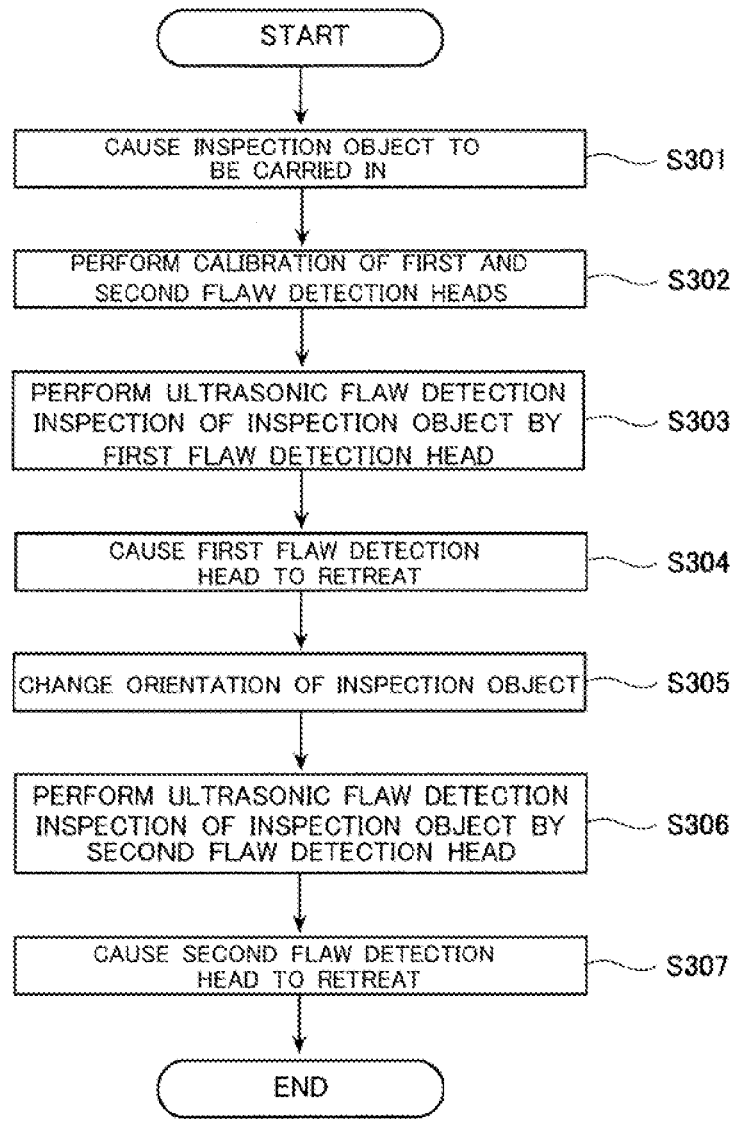
FIG. 9 is a flowchart showing one example of operations of the ultrasonic flaw detector according to Embodiment 3.

FIG. 9 is a flowchart showing one example of operations of the ultrasonic flaw detector according to Embodiment 3.

First, it is assumed that, as shown in FIG. 8, the first moving mechanism 40A and the second moving mechanism 40B of the ultrasonic flaw detector 100 are positioned at their initial positions, respectively. It is also assumed that the inspection object 31 has not been conveyed to the flaw detection area 30 of the ultrasonic flaw detector 100.

In this state, the controller 50 performs operations of the ultrasonic flaw detector 100 in a manner described below.

As shown in FIG. 9, the controller 50 causes the carry-in/out mechanism 90 to carry the inspection object 31 into the flaw detection area 30 of the ultrasonic flaw detector 100 (a carry-in/out process; step S301). While performing step S301 (the carry-in/out process), the controller 50 performs calibration of the first flaw detection head 10A and the second flaw detection head 10B (step S302).

Next, the controller 50 performs ultrasonic flaw detection inspection of the inspection object 31 by the first flaw detection head 10A in the same manner as in Embodiment 1 (step S303), and causes the first flaw detection head 10A to retreat (step S304). Then, the operator changes the orientation of the inspection object 31 (step S305).

Subsequently, the controller 50 performs ultrasonic flaw detection inspection of the inspection object 31 by the second flaw detection head 10B (step S306), and causes the second flaw detection head 10B to retreat (step S307). Then, the controller 50 performs orientation change of the inspection object 31 and ultrasonic flaw detection inspection of the inspection object 31 by the first flaw detection head 10A and/or the second flaw detection head 10B until flaw detection inspection is performed on all the portions (i.e., all the side surfaces) of the inspection object 31.

The ultrasonic flaw detector 100 according to Embodiment 3 with the above-described configuration performs calibration of the first flaw detection head 10A and the second flaw detection head 10B while the carry-in/out mechanism 90 is carrying in the inspection object 31. Accordingly, the ultrasonic flaw detector 100 according to Embodiment 3 provides the same functional advantages as those provided by the ultrasonic flaw detector 100 according to Embodiment 1.

Although in Embodiment 3 the calibration of the first flaw detection head 10A and the second flaw detection head 10B is performed while the carry-in/out mechanism 90 is carrying in the inspection object 31, the present embodiment is not thus limited. For example, calibration of only one of the first flaw detection head 10A and the second flaw detection head 10B may be performed while the carry-in/out mechanism 90 is carrying in the inspection object 31.

Although in the Embodiment 3 the operator changes the orientation of the inspection object 31, the present embodiment is not thus limited. Similar to the case of the ultrasonic flaw detector 100 according to Embodiment 2, the orientation of the inspection object 31 may be changed by the orientation changing mechanism 80.

[Variation 1]

Next, a variation of the ultrasonic flaw detector 100 according to Embodiment 3 is described. Since the configuration of an ultrasonic flaw detector 100 according to Variation 1 of Embodiment 3 is the same as that of the ultrasonic flaw detector 100 according to Embodiment 3, operations (operation method) of the ultrasonic flaw detector are described below.

[Operations (Operation Method) of Ultrasonic Flaw Detector]

Figure 10:
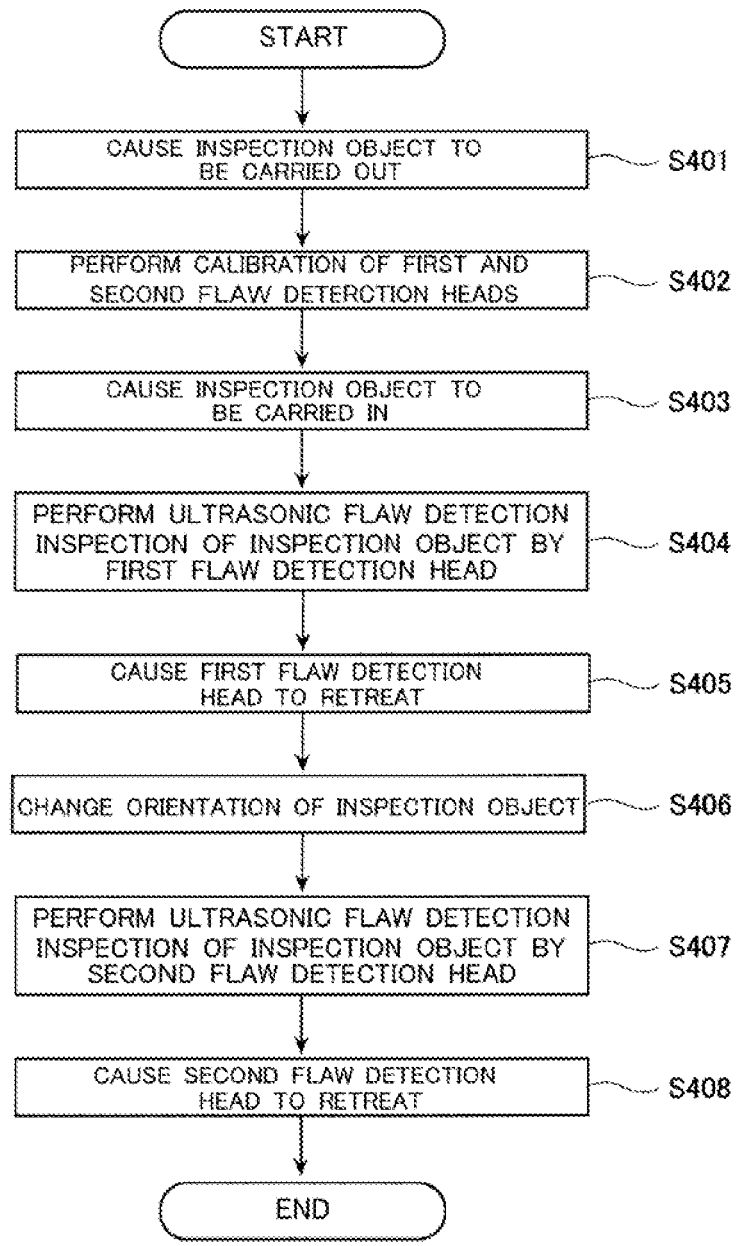
FIG. 10 is a flowchart showing one example of operations of an ultrasonic flaw detector according to Variation 1 of Embodiment 3.

FIG. 10 is a flowchart showing one example of operations of the ultrasonic flaw detector according to Variation 1 of Embodiment 3.

First, it is assumed that flaw detection inspection of the inspection object 31 disposed in the flaw detection area 30 of the ultrasonic flaw detector 100 has ended. It is also assumed that the first moving mechanism 40A and the second moving mechanism 40B of the ultrasonic flaw detector 100 are positioned at their initial positions, respectively.

In this state, the controller 50 performs operations of the ultrasonic flaw detector 100 in a manner described below.

As shown in FIG. 10, the controller 50 causes the carry-in/out mechanism 90 to carry the inspection object 31 out of the flaw detection area 30 of the ultrasonic flaw detector 100 (a carry-in/out process; step S401). While performing step S401 (the carry-in/out process), the controller 50 performs calibration of the first flaw detection head 10A and the second flaw detection head 10B (step S402).

Then, similar to Embodiment 3, the controller 50 causes the carry-in/out mechanism 90 to carry the uninspected inspection object 31 into the flaw detection area 30 of the ultrasonic flaw detector 100 (step S403). Next, the controller 50 performs ultrasonic flaw detection inspection of the inspection object 31 by the first flaw detection head 10A (step S404), and causes the first flaw detection head 10A to retreat (step S405). Then, an operator changes the orientation of the inspection object 31 (step S406).

Next, the controller 50 performs ultrasonic flaw detection inspection of the inspection object 31 by the second flaw detection head 10B (step S407), and causes the second flaw detection head 10B to retreat (step S408). Then, the controller 50 performs orientation change of the inspection object 31 and ultrasonic flaw detection inspection of the inspection object 31 by the first flaw detection head 10A and/or the second flaw detection head 10B until flaw detection inspection is performed on all the portions (i.e., all the side surfaces) of the inspection object 31.

The ultrasonic flaw detector 100 according to Variation 1 with the above-described configuration performs calibration of the first flaw detection head 10A and the second flaw detection head 10B while the carry-in/out mechanism 90 is carrying out the inspection object 31. Accordingly, the ultrasonic flaw detector 100 according to Variation 1 provides the same functional advantages as those provided by the ultrasonic flaw detector 100 according to Embodiment 1.

Although in Variation 1 the calibration of the first flaw detection head 10A and the second flaw detection head 10B is performed while the carry-in/out mechanism 90 is carrying out the inspection object 31, the present variation is not thus limited. Alternatively, for example, calibration of only one of the first flaw detection head 10A and the second flaw detection head 10B may be performed while the carry-in/out mechanism 90 is carrying out the inspection object 31. Further alternatively, after the carry-in/out mechanism 90 has carried out the inspection object 31, calibration of at least one of the first flaw detection head 10A and the second flaw detection head 10B may be performed while the carry-in/out mechanism 90 is carrying in another inspection object 31.

Although in Variation 1 the operator changes the orientation of the inspection object 31, the present variation is not thus limited. Similar to the case of the ultrasonic flaw detector 100 according to Embodiment 2, the orientation of the inspection object 31 may be changed by the orientation changing mechanism 80.

From the foregoing description, numerous modifications and other embodiments of the present invention are obvious to a person skilled in the art. Therefore, the foregoing description should be interpreted only as an example and is provided for the purpose of teaching the best mode for carrying out the present invention to a person skilled in the art. The structural and/or functional details can be substantially altered without departing from the spirit of the present invention.

INDUSTRIAL APPLICABILITY

The ultrasonic flaw detector and the method of operating the ultrasonic flaw detector according to the present invention are useful, because even in the case of inspecting an inspection object having a complex shape, the ultrasonic flaw detector and the method of operating the ultrasonic flaw detector can reduce the work time.

REFERENCE SIGNS LIST 10A first flaw detection head
10B second flaw detection head
11A mounting portion
20 calibration area
20A first calibration area
20B second calibration area
21A calibration standard sample
21B calibration standard sample
22A artificial defect
22B artificial defect
30 flaw detection area
31 inspection object
40A first moving mechanism
40B second moving mechanism
41A first moving part
41B second moving part
42A first gantry part
42B second gantry part
43A guide member
43B guide member
50 controller
60 container
70 retaining mechanism
71A arm member
71B arm member
72 container
73 connection part
80 orientation changing mechanism
81 base
82A guide
82B guide
82C guide
82D guide
83A first driver
83B second driver
84A truck
84B truck
85A arm
85B arm
86A attaching part
86B attaching part
87A gripper
87B gripper
90 carry-in/out mechanism
100 ultrasonic flaw detector

The invention claimed is:

1. An ultrasonic flaw detector comprising:
a first flaw detection head including a first probe;
a second flaw detection head including a second probe;
a moving mechanism that causes the first flaw detection head and the second flaw detection head to perform scanning;
a first calibration area in which a first calibration standard sample is disposed;
a second calibration area in which a second calibration standard sample is disposed;
a flaw detection area in which an inspection object is disposed; and
a controller that is configured to perform a second calibration process of causing the second flaw detection head to scan the second calibration standard sample to perform calibration using the second calibration standard sample either in a case where the controller performs a first calibration process of causing the first flaw detection head to scan the first calibration standard sample to perform calibration using the first calibration standard sample or in a case where the controller performs a first flaw detection process of performing ultrasonic flaw detection inspection of the inspection object by the first flaw detection head;
wherein the flaw detection area is interposed between the first calibration area and the second calibration area.

2. The ultrasonic flaw detector according to claim 1, wherein the first and second calibration standard samples are separate from each other.

3. The ultrasonic flaw detector according to claim 1, further comprising an orientation changing mechanism that changes an orientation of the inspection object, wherein
the controller is further configured to perform the second calibration process of causing the second flaw detection head to scan the second calibration standard sample to perform calibration using the second calibration standard sample when performing: the first calibration process of causing the first flaw detection head to scan the first calibration standard sample to perform calibration using the first calibration standard sample; the first flaw detection process of performing ultrasonic flaw detection inspection of the inspection object by the first flaw detection head; or an orientation changing process of changing the orientation of the inspection object by the orientation changing mechanism.

4. The ultrasonic flaw detector according to claim 3, further comprising a retaining mechanism that retains the inspection object, wherein the controller is further configured to cause the retaining mechanism to retain the inspection object when performing the first flaw detection process, and cause the retaining mechanism to release the inspection object from a state of being retained by the retaining mechanism when performing the orientation changing process.

5. The ultrasonic flaw detector according to claim 4, wherein the retaining mechanism includes a pair of arm members, and is configured to retain the inspection object by sandwiching, by the pair of arm members, both ends of the inspection object that are not subjected to the scanning.

6. The ultrasonic flaw detector according to claim 5, wherein the orientation changing mechanism is configured to change the orientation of the inspection object by gripping a portion of the inspection object, the portion being different from portions retained by the retaining mechanism, and rotating the inspection object.

7. The ultrasonic flaw detector according to claim 3, wherein the controller is further configured to perform the first calibration process and the second calibration process when performing the orientation changing process.

8. The ultrasonic flaw detector according to claim 1, further comprising a carry-in/out mechanism that carries the inspection object into or out of the flaw detection area, wherein the controller is further configured to perform the second calibration process of causing the second flaw detection head to scan the second calibration standard sample to perform calibration using the second calibration standard sample when performing: the first calibration process of causing the first flaw detection head to scan the first calibration standard sample to perform calibration using the first calibration standard sample; the first flaw detection process of performing ultrasonic flaw detection inspection of the inspection object by the first flaw detection head; or a carry-in/out process in which the carry-in/out mechanism carries the inspection object into or out of the flaw detection area.

9. The ultrasonic flaw detector according to claim 8, wherein the controller is further configured to perform the first calibration process and the second calibration process when performing the carry-in/out process.

10. The ultrasonic flaw detector according to claim 1, wherein the first flaw detection head is configured to perform ultrasonic flaw detection of a flat portion of the inspection object, and the second flaw detection head is configured to perform ultrasonic flaw detection of a curved portion of the inspection object.

11. A method of operating an ultrasonic flaw detector, the method comprising performing a second calibration process of causing a second flaw detection head to scan a second calibration standard sample to perform calibration using the second calibration standard sample either in a case of performing a first calibration process of causing a first flaw detection head to scan a first calibration standard sample to perform calibration using the first calibration standard sample or in a case of performing a first flaw detection process of performing ultrasonic flaw detection inspection of an inspection object by the first flaw detection head;

wherein:

in the first calibration process, the first flaw detection head performs calibration using the first calibration standard sample disposed in a first calibration area;

in the second calibration process, the second flaw detection head performs calibration using the second calibration standard sample disposed in a second calibration area; and in the first flaw detection process, a flaw detection area in which the inspection object is disposed is interposed between the first calibration area and the second calibration area.

12. The method of operating an ultrasonic flaw detector according to claim 11, wherein the second calibration process is performed when: the first calibration process is performed; the first flaw detection process is performed; or an orientation changing process of changing an orientation of the inspection object by an orientation changing mechanism is performed.

13. The method of operating an ultrasonic flaw detector according to claim 12, wherein a retaining mechanism retains the inspection object when the first flaw detection process is performed, and releases the inspection object from a state of being retained by the retaining mechanism when the orientation changing process is performed.

14. The method of operating an ultrasonic flaw detector according to claim 13, wherein the retaining mechanism includes a pair of arm members, and is configured to retain the inspection object by sandwiching, by the pair of arm members, both ends of the inspection object that are not subjected to the scanning.

15. The method of operating an ultrasonic flaw detector according to claim 14, wherein the orientation changing mechanism is configured to change the orientation of the inspection object by gripping a portion of the inspection object, the portion being different from portions retained by the retaining mechanism, and rotating the inspection object.

16. The method of operating an ultrasonic flaw detector according to claim 12, wherein the first calibration process and the second calibration process are performed when the orientation changing process is performed.

17. The method of operating an ultrasonic flaw detector according to claim 11, wherein the second calibration process is performed when: the first calibration process is performed; the first flaw detection process is performed; or a carry-in/out process in which a carry-in/out mechanism carries the inspection object into or out of a flaw detection area is performed.

18. The method of operating an ultrasonic flaw detector according to claim 17, wherein
the first calibration process and the second calibration process are performed when the carry-in/out process is performed.

19. The method of operating an ultrasonic flaw detector according to claim 11, wherein
the first flaw detection head is configured to perform ultrasonic flaw detection of a flat portion of the inspection object, and the second flaw detection head is configured to perform ultrasonic flaw detection of a curved portion of the inspection object.

\* \* \* \* \*